United States Patent
Pialet et al.

(10) Patent No.: US 7,297,408 B2
(45) Date of Patent: Nov. 20, 2007

(54) ANTIFOULING COATING FOR SENSOR TRANSDUCERS USED FOR MONITORING FLUID PROPERTIES

(75) Inventors: Joseph W. Pialet, Willowick, OH (US); Carlos A. Piedrahita, Mentor, OH (US); William P. Taylor, Mentor, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 220 days.

(21) Appl. No.: 10/989,979

(22) Filed: Nov. 16, 2004

(65) Prior Publication Data

US 2006/0105101 A1 May 18, 2006

(51) Int. Cl.
*B32B 9/04* (2006.01)

(52) U.S. Cl. ............ 428/447; 106/287.13; 106/287.14; 702/22; 702/25; 702/23; 73/53.05; 73/61.71; 427/387

(58) Field of Classification Search ................ 428/447; 106/287.13, 287.14; 427/387; 73/53.05, 73/61.71; 702/22, 25, 23
See application file for complete search history.

(56) References Cited

U.S. PATENT DOCUMENTS

| 6,989,625 B2 * | 1/2006 | Suzuki et al. ................ 310/334 |
| 2002/0103605 A1 * | 8/2002 | Potyrailo et al. ............. 702/22 |

FOREIGN PATENT DOCUMENTS

WO 2003/064981 * 8/2003

* cited by examiner

*Primary Examiner*—Margaret G. Moore
(74) *Attorney, Agent, or Firm*—Teresan W. Gilbert; Michael F. Esposito; Christopher D. Hilker

(57) ABSTRACT

A coating for sensor transducers that transmit a signal to—and/or receive a signal from—a fluid, either liquid or gas, in contact with the transducer. In particular the coating minimizes or eliminates fouling of the transducer surface by the fluid, reducing the need for transducer maintenance, while not interfering with the transducer's ability to send and/or receive signals.

13 Claims, 1 Drawing Sheet

ANTIFOULING COATING FOR SENSOR TRANSDUCERS USED FOR MONITORING FLUID PROPERTIES

BACKGROUND OF THE INVENTION

The present invention relates to coatings for transducers in a sensor that contact a fluid, which is defined herein as a liquid, a gas or combinations thereof, to apply signals and/or measure responses when measuring a fluid property, wherein the fluid property can be a physical or chemical quality or condition. The invention finds application on transducer surfaces, which can be metal, semi-conductors, polymers, crystalline or amorphous materials or the like, that have, or can be functionalized to have, hydroxyl sites. The invention can be used with transducers for off-line, on-line or in-line monitoring and/or analysis of fluids such as, for example, lubricants, natural and/or synthetic motor oils, standard additives and/or adjuncts, combustion engine fuels, other hydrocarbon-based fluids used in transportation and industrial applications, and the like. More specifically, the present invention relates to antifouling coatings that do not substantially interfere with the transducer's ability to apply signals to and/or measure responses from a fluid, while reducing the need for transducer maintenance, such as cleaning.

Fluids are a critical component for the proper operation of many types of devices and/or processes. For example lubricants are needed for an internal combustion engine to efficiently provide power over a long service life, metal working fluid is needed in machining equipment for rapid metal removal and maximum tool life, and vapors above liquid can be used to identify the liquid. Optimum performance is achieved when the fluid in question is of a proper quantity and quality for the application. For a particular application, a fluid preferably includes an appropriate base fluid and desired performance additives, e.g. corrosion inhibitors, friction modifiers, dispersants, surfactants, detergents, markers and the like. During use or consumption, a fluid's condition should remain within specified limits, that is, chemical and/or other fluid changes should be within proper performance specifications.

A fluid's quantity, initial quality and/or continuing condition are often determined using sensors that test particular fluid properties. Such sensors, whether used off-line, on-line, or in-line, typically have one or more transducers contacting the fluid to transmit a signal, receive a response, or both transmit a signal and receive a response. A limitation for sensors is that the transducer can be fouled by the fluid, or components of the fluid including contaminants, being tested. To alleviate a fouling problem, sensors may require regular cleaning or replacement of the transducers, often after each fluid test, in order to provide sufficiently accurate results. Fouling problems can be particularly acute with sensors that make surface dependent measurements in fluids that are "surface active". For example, an attenuated total reflectance (ATR) infrared sensor, which uses an internal-reflectance-element (IRE) in contact with a fluid to determine fluid absorption at one or more frequencies, can show substantial signal drift in a lubricant formulated to provide surface corrosion and wear protection.

While coatings, such as Teflon®, are known to be used in some applications to protect transducers from fouling, an issue with present coatings is that they can substantially interfere with a signal being sent and/or received by the transducer, thereby limiting the performance of a sensor. Typical coatings have their own IR attenuation which limits their use in IR sensor applications, and many current coatings have electrical impedance or porosity issues which limit their use in sensors that transmit or receive electrical signals. Another issue with current coatings on sensor transducers is that the coating thickness is not easily controlled. Many coatings, with desirable properties, cannot be controllably applied in a sufficiently thin layer; for example, on an ATR infrared sensor's IRE transducer the coating must be on the order of nanometers to allow the optical signal to penetrate through the coating and into the fluid. Another problem with current sensor coatings is that the coatings do not provide adequate fouling protection for the transducer. That is, the coating does not substantially decrease transducer maintenance. Therefore, there is need for an improved transducer coating that does not substantially interfere with the operation of a sensor and that provides an increased transducer maintenance-free operating period.

The present invention overcomes limitations of previous coatings for transducers used to monitor/analyze fluids. The invention is a simple, cost-effective coating that has minimal effect on signals being sent and/or received by transducers in contact with a fluid, that can be applied in a controlled thickness, and that substantially decreases or eliminates transducer fouling thereby increasing the transducer's maintenance-free operating period.

SUMMARY OF THE INVENTION

Figure 1:
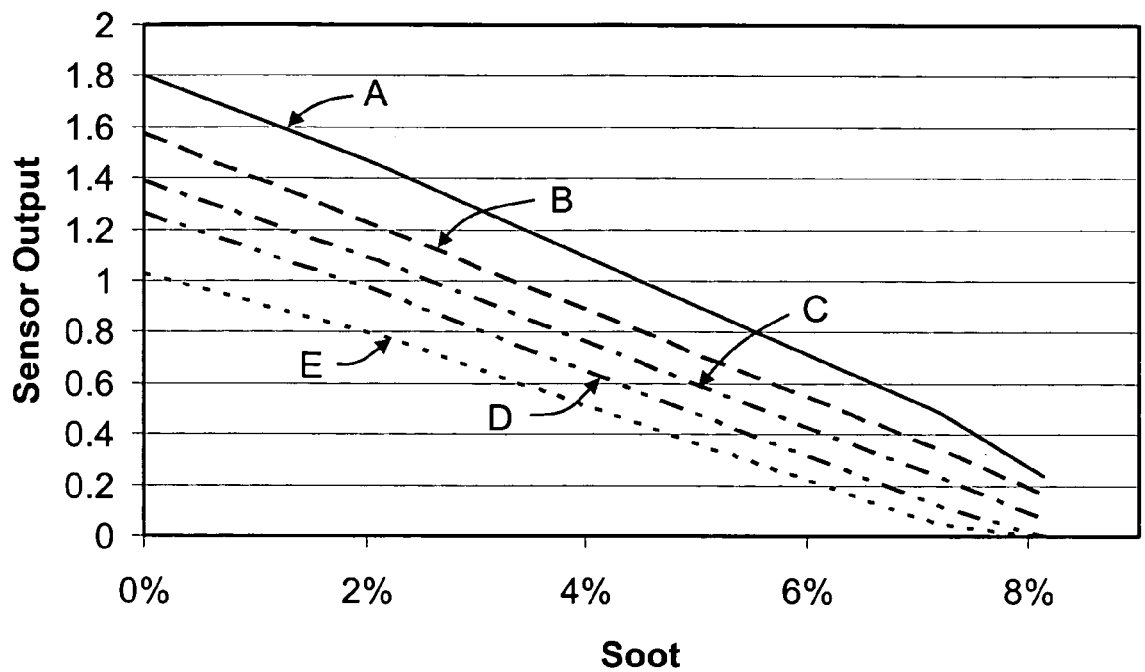
FIG. 1 is a graph showing test results for an ATR infrared sensor having an IRE transducer that does not have a coating of this invention.

The present invention is a coating for sensor transducers that are used in the measurement of a fluid property. The coating on the sensor transducer comprises at least one of an alkoxysilane, a chloro-terminated-silicone-oligomer or combinations thereof, which either may have non-hydrolysable side-chains and/or repeat-groups selected to minimize or eliminate reaction with—or wetting by—fluids or fluid components in contact with the transducer while in use, and to minimize or eliminate absorption or blocking of signals between the transducer and the fluid in contact with the transducer when in use.

A feature of the invention is that the coating can contain molecules with at least one reactive site bonded to the transducer surface and no molecule-molecule bonding, (no cross-linking or chain extension), molecules with at least one reactive site bonded to the transducer surface and molecule-molecule bonding, molecules bonded to surface-bonded molecules which are also bonded to the surface, or combinations thereof.

The invention is further a process to coat a sensor transducer, comprising:

a) cleaning the transducer surface, b) immersing the transducer into a solution selected from the group consisting of alkoxysilanes in an aqueous hydrocarbon-solvent solution, chloro-terminated-silicone-oligomers in a dry hydrocarbon solvent or combination thereof, c) rinsing the transducer with solvent, and d) drying the transducer, wherein such coated sensor transducer is used to measure/analyze fluid quality/condition.

A feature of the invention is that cleaning the transducer surface can simply remove contaminants from the surface that would interfere with an alkoxysilane or a chloro-terminated-silicone-oligomer reacting with hydroxyl sites on the transducer surface or combination thereof.

Another feature of the invention is that cleaning of the transducer surface can include functionalizing the surface by oxidation, hydrolysis or hydration to increase the number of hydroxyl sites on the transducer surface.

Another feature of the invention is that the porosity and thickness of the transducer coating can be varied by varying the number of hydroxyl sites on the transducer surface.

In an embodiment of the invention the alkoxysilanes in the solution are selected from the group consisting of monoalkoxysilanes, dialkoxysilanes, trialkoxysilanes, bis-alkoxysilanes or combinations there of.

In another embodiment of the invention the alkoxysilanes in the solution can have at least one substituent of the silicon which is an alkyl or aryl group which may optionally contain groups such as, but not limited to, fluorine, chlorine or the like.

In another embodiment of the invention the aqueous-hydrocarbon solvent in an alkoxysilane solution for immersing a transducer can be an aqueous acidic alcohol solution.

In another embodiment of the invention the chloro-terminated-silicone-oligomers in the solution are short silicone oligomers selected from the group consisting of having at least one reactive chloro group at one end, at least one reactive chloro group at both ends, at least one reactive chloro group on at least one internal silicon, or a combination thereof.

In another embodiment of the invention the chloro-terminated-silicone-oligomers in the solution can be functionalized with alkyl or aryl groups which may optionally contain groups such as, but not limited to, fluorine, chlorine or the like.

Another feature of the invention is that the alkoxysilane or the chloro-terminated-silicone-oligomer is selected from the group consisting of optimizing signal transmission from—or reception by—the sensor transducer when used to measure/analyze a fluid property, to minimizing reaction with—or wetting by fluids or fluid components in contact with the transducer when in use and combinations thereof.

Another feature of the invention is that the porosity and thickness of the transducer coating can be controlled during immersing the transducer by controlling one of the variables in group consisting of length of time that the transducer is immersed in the solution, concentration of the solution, the temperature of the solution or combinations thereof.

Another feature of the invention is that the solution for immersing the transducer can have a concentration of about 0.1% to about 10%.

Another feature of the invention is that the solution for immersing the transducer can have a concentration of about 0.5% to about 5%.

Another feature of the invention is that the transducer can be dried under ambient to elevated conditions to remove solvents used during immersing and rinsing and then dried at elevated temperature for dehydration of the coating to maximize cross-linking between remaining reactive sites of the coating.

In another embodiment of the invention the porosity and thickness of the transducer coating can be varied by a process that comprises:

a) cleaning the transducer surface, b) immersing the transducer into a solution selected from the group consisting of alkoxysilanes in an aqueous hydrocarbon-solvent solution, chloro-terminated-silicone-oligomers in a dry hydrocarbon solvent or combination thereof, c) rinsing the transducer with solvent, d) drying the transducer to remove the solvent, but not maximize cross-linking between remaining reactive sites of the coating, e) repeating steps b, c and d until the desired coating porosity and/or thickness is achieved; and f) drying the transducer to maximize cross-linking between remaining reactive sites of the coating.

DETAILED DESCRIPTION OF THE INVENTION

The invention relates to a cost-effective antifouling coating, and method of application, for sensor transducers that does not interfere with the transducer's ability to transmit signals to—and/or receive signals from—the fluid when monitoring/analyzing a quality/condition of the fluid. In particular, the invention relates to functionalized alkoxysilanes or chloro-terminated-silicone-oligomers that bond to reactive sites on the transducer surface and cross-link to form a coating, where the alkoxysilanes or chloro-terminated-silicone-oligomers are selected to minimize or eliminate 1) reaction with—or wetting by—fluids in contact with the transducer while in use, 2) absorption or blocking of signals between the transducer and the fluid in contact with the transducer when in use and 3) combinations thereof.

The transducers have reactive hydroxyl sites, (—OH groups) on the surface for bonding of the functionalized alkyoxysilanes, chloro-terminated-silicone-oligomers or combination thereof. Most transducers have surfaces made of metal, semi-conductor, polymer, crystalline or amorphous materials or the like, which may have or can have hydroxyl sites. The coating bonds to the surface and can have varying thickness and percent coverage, porosity, depending on the density of the reactive sites on the transducer surface, the selected functionalized alkoxysilane or chloro-terminated-silicone-oligomer and the process variables when applying the coating.

Examples of functionalized alkoxysilanes that that are useful for coating an IRE transducer in an ATR infrared sensor used to determine an infrared quality/condition of a hydrocarbon lubricant include but are not limited to:

a. Methyltriethoxysilane as represented by the formula:

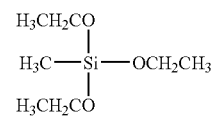

wherein $H_3C$— is a non-hydrolysable side-chain, b. (3,3,3-trifluoropropyl)trimethoxysilane as represented by the formula:

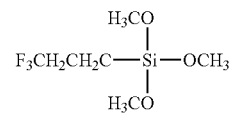

wherein F$_3$CH$_2$CH$_2$C— is a non-hydrolysable side-chain.

Examples of functionalized chloro-terminated-silicone-oligomers that are particularly useful for coating an IRE transducer in an ATR infrared sensor include but are not limited to:

a. Aquaphobe™ CM (available from Gelest Inc. of Morrisville, Pa.) as represented by the formula:

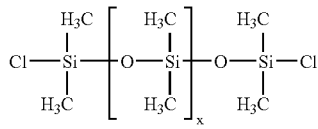

wherein the repeat group is

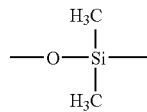

and wherein x is in the range of 0 to about 25, preferably in the range of 0 to about 10 and more preferably in the range of 0 to about 5 and H$_3$C are non-hydrolysable side-chains, b. Aquaphobe™ CF (available from Gelest Inc. of Morrisville, Pa.) which is represented by or similar to the formula:

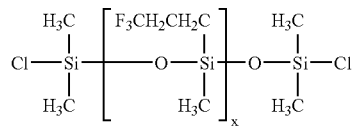

wherein x is in the range of 0 to about 25, preferably in the range of 0 to about 10 and more preferably in the range of 0 to about 5 and wherein the repeat group is

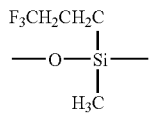

and H$_3$C and F$_3$CH$_2$CH$_2$C are non-hydrolysable side-chains.

Selection of a particular alkoxysilane or chloro-terminated-silicone-oligomer is determined by desired thickness and/or porosity of the coating, the antifouling characteristics that the material has as a coating in a particular fluid, by the particular characteristics that the material has as a coating for allowing appropriate signals to pass through the coating, between transducer and fluid, with minimal or no absorption of blockage and combinations thereof.

The number of reactive sites on the alkoxysilane or chloro-terminated-silicone-oligomer is a variable in achieving a desired coating thickness and/or porosity. A monoalkoxysilane or a silicone-oligomer terminated at only one end with a chlorine will form a single bond to a transducer surface and is then not able to form bonds to other molecules. Therefore, the coating with a molecule having only one reactive site will be only one molecule thick and, depending on the density of sites on the transducer surface, the coating can be quite porous. A dialkoxysilane or a silicone-oligomer terminated with two chlorines, typically at each end but can include chlorine substitution on internal silicon atoms, can bond to two sites on the transducer surface or can form relatively long chains of molecules that can bond at both ends to sites on the transducer surface, allowing for increased coating thickness and/or bridging of the transducer surface between reactive hydroxyl sites to decrease the coating porosity. A trialkoxysilane or a silicone-oligomer substituted with greater than two chlorines allows not only for bonding to the transducer surface and for greater molecular length, but for cross-linking between the molecules forming the coating on the transducer surface. Cross-linking allows for further increases in thickness and/or reduced porosity of the coating. Ultimately, however, the reactivity of the alkoxysilanes or chloro-terminated-silicone-oligomers must be selected to minimize reactive site remaining on the coating so that the antifouling properties of the coating are maximized.

To have good antifouling characteristics in a particular fluid, the coating must have a low surface energy relative to all fluid components, including contaminants, so that the surface is not easily wet by any the fluid components. Also the side-chains/repeat-groups of the silane or chloro-terminated-silicone-oligomer must be poor solvents for contaminants in the fluid. For example, a silane or chloro-terminated-silicone-oligomer with an amine side-chain/repeat-group would not be a good choice for use in a fluid that might have an acidic contaminant.

To minimize signal absorption or blockage of signal between transducer and fluid, the coating needs to have a side-chains and/or repeat-groups selected based on the type of signal (e.g. optical, electrical, acoustic and the like) passing between transducer and fluid. For examples, the coating for an IR sensor has minimal absorption at the frequencies of interest, the coating for an electrical impedance sensor has appropriate electrical impedance at the frequencies of interest, and the coating for an acoustic sensor has appropriate acoustic impedance at the frequencies of interest. Another element to consider when selecting the correct alkoxysilanes or chloro-terminated-silicone-oligomers is whether the material can be applied to the transducer surface to form a coating of desired appropriate thickness and/or porosity to minimize signal absorption or blockage while achieving the desired antifouling properties.

Alkoxysilanes are generally less reactive than chloro-terminated-silicone-oligomers, typically require hydrolysis, are easier to use to build up multiple layers and are less likely to bridge areas of the surface lacking hydroxyl groups. The chloro-terminated-silicone oligomers are more reactive, do not typically require hydrolysis, are more likely to bridge areas on the surface lacking hydroxyl groups, more difficult to use to build up multiple layers and generate corrosive HCl during reaction.

The present invention forms appropriate coatings of alkoxysilanes or chloro-terminated-silicone-oligomers on fluid quality/condition sensor transducers. In one embodiment the process has four steps which are described in the following.

The first process step is cleaning the transducer surface to remove hydrocarbons or other contaminants on the surface of the transducer introduced during a manufacturing process or during transducer storage and/or handling. Depending on the transducer-surface material, cleaning can be by any known process that removes contaminants; those processes include but are not limited to processes that are typically used when coating a surface with, for example, a paint or other protective or functional material. Such cleaning typically includes but are not limited to solvents, detergents or mixtures thereof, either with or without physical agitation or scrubbing, but can also include known chemical or physical processes that can clean or modify the surface. In cases where the transducer surface does not have a desired density of hydroxyl sites, the cleaning process may include but not limited to use of an oxidizer, as are known in the art, which creates additional reactive sites in addition to cleaning the surface.

After cleaning the next coating process step is immersing the transducer in a solution of either alkoxysilane in an aqueous hydrocarbon-solvent solution or a chloro-terminated-silicone-oligomer in a dry hydrocarbon solvent. Alkoxysilanes contain Si—OR groups, which hydrolyze to Si—OH in the presence of water. Chloro-terminated-silicone-oligomers contain Si—Cl groups that can react with hydroxyl sites on the transducer surface to form covalent bonds. There is also competition in the solution for the active alkoxysilane and chloro-terminated-silicone-oligomer groups to bond with other active groups both on molecules still in the solution, and, in the case where there is more than one reactive site per molecule, on molecules that have already bonded to the surface. Bonding between molecules in the solution effectively reduces the concentration of active molecules in solution and limits the useful life of the solution for transducer surface coating. Bonding between molecules with at least one molecule bonded to the transducer surface can increase coating thickness and/or reduce coating porosity. The uniformity and density/porosity of the coating bonded to the transducer surface is affected by the distribution and density of available hydroxyl sites. The thickness and porosity of the coating on the transducer coating is affected by, as already described, the number or reactive sites on the molecules, and by the concentration of the solution, the temperature of the solution and length of time that the transducer is left in the solution. The concentration alkoxysilane or chloro-terminated-silicone-oligomer in the solution is in the range of about 0.05 to about 20% preferably in the range of about 0.1 to about 10%, and is more preferably in the range about 0.5 to about 5%. In the case of the aqueous hydrocarbon-solvent solution for the alkoxysilane solution, an aqueous acidic alcohol solution is preferred. The temperature of the solution for immersing the transducer is can vary over a wide range from the freezing temperature to the boiling temperature of the solution; however, a temperature near ambient temperature is preferred for ease of processing. The time of transducer immersion is determined by the temperature of the solution and the desired coating thickness/density, but is limited, as described above, by the reactions between the molecules in solution that impede the addition of molecules to the surface of the transducer. In general, immersion times on the order of about 1 to about 60 minutes, in another embodiment about 1 to about 10 minutes.

The third step of the process is rinsing the transducer surface with solvent to remove individual or multiple alkoxysilanes or chloro-terminated-silicone-oligomer molecules that are not bonded to the surface. The solvent includes but is not limited to the same solvent used in the solutions for coating the transducer or can be one or more other solvents that are known in the art to be useful for a rinsing process. Rinsing time is a function of the solvent, the temperature of the solvent and the thickness and porosity of the coating on the transducer surface. Transducers coated with chloro-terminated-silicone-oligomers typically require longer rinse times than alkoxysilanes due to the relative size of the oligomers. In general, however, rinsing times can be on the order of about 1 to about 60 minutes, in another embodiment about 1 to about 10 minutes.

The fourth step of the process is drying the transducer surface. The drying process, which can occur in the range of at ambient to an elevated temperature, involves removing solvent from the coating on the transducer surface. The drying process also involves bonding any reactive alkoxysilane or chloro-terminated-silicone-oligomer sites that remain after the immersion and the rinsing steps of the process. In general, the chloro-terminated-silicone-oligomers, which are more reactive than alkoxysilanes, will have mostly reacted by the drying process and ambient temperature drying is typically sufficient to maximize the properties of a transducer coating using chloro-terminated-silicone-oligomers. The coating using the less reactive dialkoxysilanes, trialkoxysilanes, and/or bis-alkoxysilanes however, will typically have better coating properties if either the entire or at least the final portion of the drying process occurs at an elevated temperature to minimize the remaining reactive sites in the coating. Therefore, the preferred drying process for a transducer coated with alkoxysilanes, other than monoalkoxysilanes, includes completing the drying at elevated temperature, with the drying temperature being limited to temperatures that do not damage the coating or substrate. Silicone-oligomers that are substituted with greater than one chlorine may also benefit with final drying at elevated temperature after any remaining unreacted Si—Cl groups have had a chance to hydrolyze. Actual drying time required for any of the coatings is a function of alkoxysilane or the chloro-terminated-silicone-oligomer used for the coating, and of the drying temperature and other process variables. As an example, a transducer with a trialkoxysilane coating that was air dried overnight to remove the rinsing solvent was dried at about 60° C. and for about 4 hours to maximize cross-linking of the trialkoxysilanes.

Coatings produced with alkoxysilanes or chloro-terminated-silicone-oligomers that have more than one reactive site per molecule may not be fully reacted, especially for the alkoxysilanes, after rinsing step of the transducer coating process. In one embodiment of the invention a thicker coating can be formed on fluid-property-sensor transducers by a second process that also has a first step of cleaning the transducer surface, a second step of immersing the transducer into a solution that includes but is not limited to dialkoxysilanes, trialkoxysilanes and/or bis-alkoxysilanes in an aqueous hydrocarbon-solvent solution or silicone-oligomers with at least two chloro-terminations in a dry hydrocarbon solvent, and a third step of rinsing the transducer surface. In this embodiment, however, the transducer is not fully dried in a fourth step to maximize bonding of the remaining reactive sites, but instead is either 1) immersed into a second solution of the type described for the second step of the process, or 2) if the solvent used to rinse the transducer after the previous coating is different than that used in a second solution, the transducer is dried to only remove the rinsing solvent before immersing the transducer into the second solution of the type described for the second step of the process. The second immersion is used to increase coating thickness and/or decrease coating porosity on the transducer surface. After this second immersion step, the process has a rinsing step to again to remove alkoxysilanes or chloro-terminated-silicone-oligomers or chains of alkoxysilanes or chloro-terminated-silicone-oligomers that are not bonded to the surface during the second immersion and a drying step to remove the rinsing solvent and to minimize remaining reactive sites in the coating.

In other embodiments additional immersion, rinse, and, if needed solvent dry steps can be added before the transducer is finally dried to minimize remaining reactive sites to achieve a coating thickness/porosity that has the desired antifouling properties without substantially interfering with the transducer's ability to transmit or receive signals from a fluid.

EXAMPLES

Example A

Shown in FIG. 1 is the output of an ATR infrared sensor designed to measure the soot content of a fluid. Line A is the sensor output for a first run of testing fluid samples where the IRE transducer of the sensor was clean at the start of the run and where the soot content of the tested samples increased from essentially 0% soot to approximately 8% soot as determined by a separate analytical method that is an industry standard to determining soot in a fluid. Lines B, C D and E are the sensor output for subsequent runs of testing the same fluid samples where the sensor's IRE transducer was not cleaned between runs. While lines A through E should be essentially the same for both runs, the figure shows that the sensor output decreased with each subsequent run. When the IRE was cleaned and the sensor rerun, the sensor output returned to about the output of line A, indicating that the IRE was fouled by the soot containing fluid.

Figure 2:
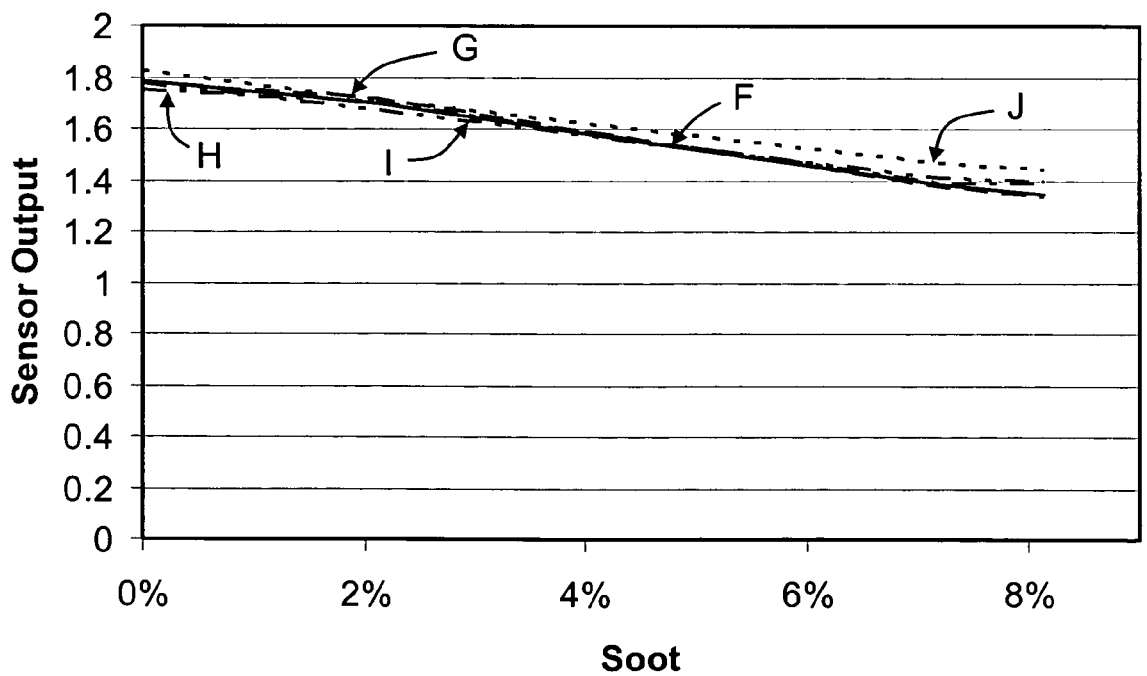
FIG. 2 is a graph showing test results for an ATR infrared sensor having an IRE transducer that does have a coating of this invention.

Shown in FIG. 2 is the output of an ATR infrared sensor similar to that used to generate the outputs shown in FIG. 1 except that the sensor's IRE was coated in the following manner. The IRE was cleaned using heptane. A solution of water in isopropyl alcohol (5/95) by volume was adjusted to a pH of approximately 5 with acetic acid. Methyltriethoxysilane was added to form about a 2% solution and allowed to hydrolyze for about 5 minutes with gentle agitation. The IRE was suspended in the solution for about 5 minutes. The part was rinsed with isopropyl alcohol and allowed to air dry overnight. The IRE was then dried in a forced draft oven at approximately 60 C. for about 4 hours. Line F is the sensor output for a first run using the same soot containing sample fluids described above. Lines G, H, I, J are the sensor output for subsequent runs of testing the fluid samples where the sensor's IRE transducer was not cleaned between runs. The output for the individual runs were about the same and cleaning the lens showed essentially no change in sensor output when an additional run was made, indicating that the coated IRE of the sensor used for FIG. 2 had relatively minor fouling when compared to the fouling shown in FIG. 1 for the sensor with the uncoated IRE. Therefore, the sensor of FIG. 2 with the coated IRE provided better performance with less need for maintenance than the sensor with the uncoated IRE of FIG. 1.

Example B

Results similar to those, shown in FIGS. 1 and 2 were produced by ATR infrared sensors that had uncoated and coated IRE transducers respectively where the coated IRE was produced by the following process. The IRE was cleaned using heptane. A solution of water in isopropyl alcohol (5/95) by volume was adjusted to a pH of approximately 5 with acetic acid. (3,3,3-trifluoropropyl)trimethoxysilane was added to form about a 2% solution and allowed to hydrolyze for about 5 minutes with gentle agitation. The IRE was suspended in the solution for approximately 5 minutes. The IRE was rinsed with isopropyl alcohol and allowed to air dry overnight. The part was then dried in a forced draft oven at approximately 60 C. for about 4 hours.

Example C

Results similar to those shown in FIGS. 1 and 2 were produced by ATR infrared sensors that had uncoated and coated IRE transducers respectively where the coated IRE was produced by the following process. The IRE was cleaned using heptane. An α,ω dichloro dimethylsiloxane oligomer (Aquaphobe CM obtained from Gelest Inc.) was added to dry heptane to form about a 2% solution. The IRE was suspended in the solution for approximately 5 minutes. The IRE was rinsed in heptane and allowed to air dry overnight. The part was then dried in a forced draft oven at approximately 60 C. for about 4 hours.

Example D

Results similar to those shown in FIGS. 1 and 2 were produced by ATR infrared sensors that had uncoated and coated IRE transducers respectively where the coated IRE was produced by the following process. The IRE was cleaned using heptane. An α,ω dichloro fluoroalkylmethylsiloxane oligomer (Aquaphobe CF) was added to dry heptane to form a 2% solution. The IRE was suspended in the solution for approximately 5 minutes. The part was rinsed in heptane and allowed to air dry overnight. The IRE was then dried in a forced draft oven at approximately 60 C. for about 4 hours.

Although the invention has been shown and described with respect to certain embodiments, it is obvious that equivalent alterations and modifications will occur to others skilled in the art upon reading and understanding of the specification. The present invention includes all such equivalent alterations and modifications, and is limited only by the scope of the claims.

What is claimed is:

1. A coating made from a solution comprising an alkoxysilane which is a coating on a transducer of a sensor used to measure a fluid property; wherein the coating has antifouling properties that do not substantially interfere with the transducer's ability to measure fluid properties, allowing contact of the fluid and contaminants in the fluid with the sensor itself while preventing said contact from fouling the sensor;

wherein the coating is prepared from a solution containing alkoxysilanes, wherein the alkoxysilanes are selected from the group consisting of:

a. (3,3,3-trifluoropropyl)trimethoxysilane as represented by the formula:

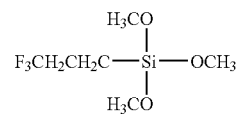

wherein $F_3CH_2CH_2C-$ is a non-hydrolysable side-chain or b. a combination of (3,3,3-trifluoropropyl)trimethoxysilane and methyltriethoxysilane, where the methyltriethoxysilane is represented by the formula:

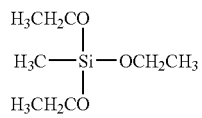

wherein H₃C— is a non-hydrolysable side-chain.

2. The coating of claim 1 wherein the alkoxysilanes bond to reactive sites on the transducer surface to form a coating and wherein the alkoxysilanes are selected from the group so as to (1) minimize or eliminate reaction with—or wetting by—fluids in contact with the transducer while in use; (2) minimize or eliminate absorption or blocking of signals between the transducer and the fluid in contact with the transducer when in use or (3) combinations thereof.

3. The coating of claim 1 wherein the transducer has reactive hydroxyl groups on the surface for binding with the coating consisting of functionalized alkoxysilanes.

4. The coating of claim 1 wherein the transducer's surface is selected from the group consisting of metal, semi-conductor, polymer, crystalline, amorphous materials, hydroxyl sites and combinations thereof.

5. The coating of claim 1 wherein the coating contains molecules comprising alkoxysilane molecules, where said molecules are bonded to the transducer surface and/or other molecules by a means selected from the group consisting of: molecules with at least one reactive site bonded only to the transducer surface and no molecule-molecule bonding; molecules with at least one reactive site bonded to the transducer surface and/or other molecules by molecule-molecule bonding; molecules with at least one reactive site bonded to one or more other molecules, at least one of which is bonded to the surface of the transducer or bonded to a molecule that is; and combinations thereof.

6. A process to make a sensor transducer antifouling coating comprising (a) cleaning a transducer surface; (b) immersing the transducer into a solution selected from the group consisting of alkoxysilanes; (c) rinsing the transducer with solvent; (d) drying the transducer to remove the solvent and to minimize remaining reactive sites of the coating resulting in antifouling coating on the transducer of the sensor; wherein the drying temperature occurs at about ambient temperature to about 60° C. so as to not damage the substrate on the coating.

7. The process of claim 6 wherein the solution for immersing the transducer has a concentration in the range of about 0.1% to about 10%.

8. The process of claim 6 wherein a cleaning material is used to clean to transducer surface and is selected from the group consisting of solvents, detergents, oxidizers, physical agitation, scrubbing, and combinations thereof resulting in cleaning and modifying the surface of the transducer.

9. The process of claim 6 wherein the immersion time is in the range of about 1 minute to about 60 minutes at a temperature in the range of ambient temperature to elevated temperature.

10. The process of claim 6 wherein the coating has anti-fouling properties that do not substantially interfere with the transducer's ability to transmit or receive signals from a fluid.

11. A process to make a sensor transducer antifouling coating comprising (a) cleaning a transducer surface; (b) immersing the transducer into a solution selected from the group consisting of alkoxysilanes; (c) rinsing the transducer with solvent; (d) drying the transducer to remove the solvent but not to minimize remaining reactive sites of the coating; (e) repeating steps (b), (c), and (d) until the desired coating porosity and thickness is achieved; and (f) drying the transducer to minimize remaining reactive sites of the coating resulting in antifouling coating on the transducer of the sensor.

12. The process of claim 11 wherein the coating has anti-fouling properties that do not substantially interfering with the transducer's ability to transmit or receive signals from a fluid.

13. A sensor comprising a transducer element capable of measuring a fluid property and a coating made from a solution comprising an alkoxysilane; wherein the coating has anti-fouling properties that do not substantially interfere with the transducer's ability to measure fluid properties, allowing contact of the fluid and contaminants in the fluid with the sensor itself while preventing said contact from fouling the sensor; and wherein the sensor is an ATR infrared sensor or an IRE transducer.

* * * * *